United States Patent [19]

Huszczuk

[11] Patent Number: 4,680,956

[45] Date of Patent: Jul. 21, 1987

[54] RESPIRATORY ANALYZER CALIBRATION APPARATUS WITH CONTROLLED RESPIRATORY GAS EXCHANGE SIMULATION

[75] Inventor: Andrew R. Huszczuk, Long Beach, Calif.

[73] Assignee: Research and Education Institute, Inc. Harbor-UCLA Medical Center, Torrance, Calif.

[21] Appl. No.: 842,924

[22] Filed: Mar. 24, 1986

Related U.S. Application Data

[62] Division of Ser. No. 552,615, Nov. 17, 1983, abandoned.

[51] Int. Cl.$^4$ .................... G01N 33/497; G01D 25/00
[52] U.S. Cl. .................................................. 73/1 G
[58] Field of Search ................. 73/1 G, 432 J, 432 V, 73/432 R, 866.4, 865.9, 432.1; 128/716, 719

[56] References Cited

U.S. PATENT DOCUMENTS

| | | | |
|---|---|---|---|
| 3,943,775 | 3/1976 | DeBaun | 73/432 R |
| 4,448,058 | 5/1984 | Jaffe et al. | 73/1 G X |
| 4,509,359 | 4/1985 | Gedeon et al. | 73/1 G X |
| 4,516,424 | 5/1985 | Rowland | 73/1 G X |
| 4,537,058 | 8/1985 | Luper | 73/1 G |

OTHER PUBLICATIONS

"A Piston Pump for Respiration Simulation"; *J. Appl. Physioli Respirat. Environ. Exercise Physiol.*; 50(3); pp. 663-664, 1981, U. Boutellier et al.

*Primary Examiner*—Tom Noland
*Attorney, Agent, or Firm*—Drucker & Sommers

[57] ABSTRACT

A method and apparatus for the controlled simulation of respiratory gas exchange as it takes place in mammals, for the primary purpose of calibrating and checking the performance of laboratory and clinical test equipment systems. The method and apparatus can reproduce any range of respiratory performance by pumping and mixing atmospheric air with a gas mixture of carbon dioxide and nitrogen. The subject matter of the disclosure provides an accurate, economical and rapid means of on-line calibration of analytical respiratory test systems.

11 Claims, 1 Drawing Figure

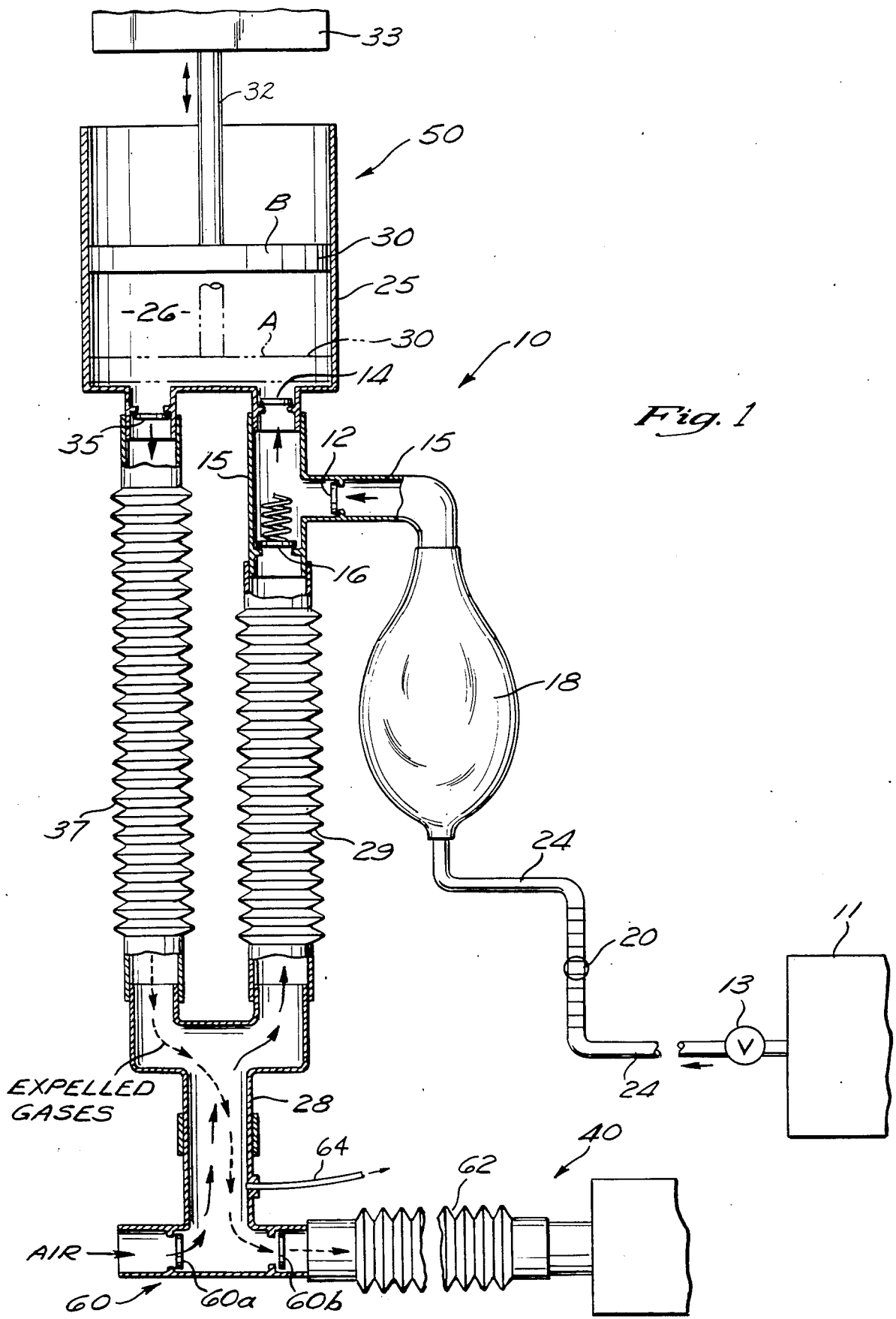

… …

RESPIRATORY ANALYZER CALIBRATION APPARATUS WITH CONTROLLED RESPIRATORY GAS EXCHANGE SIMULATION

This application is a division of application Ser. No. 552,615, filed Nov. 17, 1983, and now abandoned.

BACKGROUND OF THE INVENTION

1. Scope of the Invention

The present invention relates to an apparatus which can simulate any respiratory function in mammals for the purpose of calibrating analytical systems. The simulation is accomplished by a piston pump which "inhales" surrounding atmospheric air, composed approximately of 21% (by volume) oxygen and 79% nitrogen, and mixing said atmospheric air in varying proportions, with a pre-mixed volume of carbon dioxide and nitrogen, then "exhaling" the pre-determined gas mixture to simulate a particular respiratory performance evaluated by the test system to be calibrated.

Respiratory function can theoretically range from zero oxygen conversion (all oxygen inhaled is exhaled) to nearly total oxygen conversion (no free oxygen is exhaled). An approximation of total oxygen conversion can be found in nature in diving whales that can hold their breaths for as long as 45 minutes, during which time most of the oxygen is consumed. The exhaled gases of these diving whales approximate a mixture of about 17% carbon dioxide, by volume, in nitrogen.

The present invention utilizes a mixture of gases which in composition approximates a gas that a diving whale would exhale after total oxygen depletion. By diluting the gas mixture with a pre-determined amount of atmospheric air, any range of respiratory function can be simulated in a known mixture of "exhaled" $O_2$—$CO_2$—$N_2$ gas. By comparing the known parameters of the respiratory simulator with the results given by the analytical respiratory equipment being calibrated, the accuracy of such analytical equipment can be verified.

2. Prior Art

Prior to the use of respiratory simulators, in order to calibrate an analytical respiratory equipment system, a biological subject would have its expired gases collected at the outlet of said system and subjected to tedious classical analyses and manual calculations. The variables of respiration of this subject monitored by the laboratory or clinical test system and results of said analysis would be compared. This type of calibration was crude at best since the biological subject could not produce uniform, controlled, respiration and metabolic rate.

A respiratory simulator has also been previously developed, by others, to simulate inspiration and expiration using a double piston pump (*A Piston Pump for Respiration Simulation;* U. Boutellier, U. Gomez, and G. Mader; J. Appl. Physiology, 50(3): 663–664, 1981). The Boutellier et al double piston simulator utilizes one cylinder as the inspiratory chamber, "inhaling" atmospheric air, while the other cylinder acted as the expiratory chamber, "exhaling" a pre-mixed $O_2$—$CO_2$—$N_2$ gas mixture. While this system provides on-line analysis of known volumes and compositions of gases, it requires the use of an expensive pre-mixed gas for the calibration. Because the pre-mixed gas mixture was solely used as the expiratory gas, only one composition of expired gas could be used for calibration purposes. To vary compositions, different tanks of pre-mixed $O_2$—$CO_2$—$N_2$ gases of exact known compositions would be required, and this approach to on-line calibration thus becomes very expensive.

In general, the invention relates to a respiratory simulator that replaces biological subjects to test the accuracy and calibrate the performance of respiratory analysis equipment. The simulation of respiration is accomplished by a single cylinder piston pump that inhales atmospheric air and mixes it with a calibration gas composed of $CO_2$ and $N_2$. The pump then "exhales" the mixture of gases at known concentrations and known frequencies and volumes and compares the results given by the analytical equipment. The present invention thus allows simplified on-line automatic calibration of respiratory and metabolic analysis equipment over a wide range of exhalation products.

SUMMARY OF THE INVENTION

The present invention simplifies the Boutellier et al. apparatus by providing a single chambered piston pump. Furthermore, only one tank of a calibrating gas mixture is required, the calibrating gas mixture initially containing no oxygen and about 17% $CO_2$ in $N_2$, by volume. Such zero oxygen calibrating mixture simulates maximum oxygen utilization or maximum oxygen efficiency on the respiration cycle. The calibrating mixture parameters are readily varied to simulate any other (desired) levels of gas exchange by introducing a given volume of air into the individual calibrating gas mixture.

Also, the volume of the calibrating $CO_2$—$N_2$ gas mixture initially required is reduced by about 75% since the mixture is diluted by cost-free atmospheric air. Indeed, the cost of purchasing the initial $CO_2$—$N_2$ gas mixture can be further reduced by introducing the $CO_2$ and $N_2$ into the simulator from separate tanks and mixing just prior to entering the respiratory apparatus. The present invention thus reduces calibration time from hours to minutes, and greatly reduces the cost of expensive premixed gases.

DETAILED DESCRIPTION OF THE INVENTION

The respiratory simulation apparatus of this invention is shown schematically in FIG. 1 and is designated generally by the numeral 10. The apparatus comprises a calibration gas source, e.g. tank 11 which contains preferably a pre-mixed, commercially available source of carbon dioxide ($CO_2$) in nitrogen. Typically, a 17% mixture of $CO_2$ in $N_2$, by volume, is introduced into tank 11. However, a range of mixtures of 15–20% $CO_2$ in $N_2$, by volume, can be initially introduced into tank 11 as the calibration gas.

The pre-mixed calibration gases are fed, via calibration tank outlet valve 13, to inlet conduit pipe 24, and thence to a flexibly-walled collapsible bag or bladder 18, via a rotameter 20. In this manner, the calibration gas is introduced to the bladder 18 at a controlled and monitored flowrate and known composition. Alternatively, separate $CO_2$ and $N_2$ tanks can feed these gases to the bladder 18 through conventional rotometer devices to achieve a pre-mixed gas in the bladder. The bladder 18 serves as a temporary storage medium for the calibration gas, the gas residing temporarily in bladder 18 at atmospheric pressure.

The calibration gas is drawn into a piston chamber 26 as follows. The upward stroke of the piston 30 in piston chamber 26 (powered by reciprocating device 33), simulates the inhalation phase of respiration and the downward piston stroke simulates the exhalation phase of respiration. During the upward stroke of the piston 30 within piston cylinder 25 from position A to position B, the pressure in chamber 26 is reduced and the calibration gas is sucked into the piston chamber 26 through conventional one-way pressure valves 12 and 14 automatically opening under any pressure differential set up between bladder 18 and chamber 26 during the upward stroke of piston 30. Thus, the $CO_2$–$N_2$ calibration gas commences to enter the single piston chamber 26 of piston cylinder 25 as the upward stroke of piston 30 commences.

As soon as the bladder 18 is essentially evacuated, e.g. to 5–10 cm of water below atmospheric pressure, spring-loaded valve 16 in conduit 15 is pre-set to open, thereby allowing atmospheric air to enter piston chamber 26 via inspiratory port 60a of a conventional two-way breathing valve 60 usually constituting the initial stage of the analyzer 40 being tested. Breathing valve 60 is usually affixed to mouthpiece or facemask interface 28 of the respiratory apparatus of this invention. The air then passes through corrugated tube or means 29, valves 16 and 14, and mixes with the previously introduced, known quantity of $CO_2$ and $N_2$ in piston chamber 26.

The volume of gas entering piston chamber 26 (which is equivalent to the inhalation phase of the respiratory cycle) is controlled by the extent of stroke displacement of the piston 30 within piston cylinder 25. Thus, the piston 30 is provided with a piston rod 32, connected for reciprocal movement to a conventional reciprocating device 33. The reciprocating device 33 controls the stroke displacement of the piston rod 32 and thereby the volume of the chamber 26 within piston cylinder 25. The stroke displacement of piston rod 32 is made variable by conventional means, as is the frequency of reciprocation of the piston rod 32 and its associated piston 30.

The upward stroke displacement of piston 30 is followed by a downward stroke displacement of piston 30 under the influence of reciprocal power means 33. The downward stroke simulates the exhalation phase of the respiratory cycle, and during the exhalation phase, the mixture of $O_2$, $CO_2$ and $N_2$ are expelled through one-way outlet valve means 35, through a corrugated conduit pipe or means 37, to a tested respiratory metabolic analysis system 40, shown schematically in FIG. 1.

During the downward stroke of piston 30, calibration gas continues to flow, via line 24, under a controlled and monitored flowrate to bladder 18 so that, during the exhalation phase of the piston cycle, the bladder 18 is again filled with a known volume or amount of calibration gas. And upon commencement of the upward (rearward) stroke of the piston 30, the calibration gas will be "sucked in" to the chamber 26, to repeat the respiratory cycle, as previously described.

The rate of bleeding of calibration gas to the bladder 18, the extent of stroke displacement, and frequency of displacement of piston 30 are all readily altered to simulate a variety of metabolic and respiratory states of a biological subject.

OPERATION OF THE SIMULATED RESPIRATION APPARATUS

During the phase of the pump cycle simulating inhalation, piston 30 is upwardly drawn (as shown in FIG. 1) from dotted line position A to solid line position B in piston cylinder 25, providing reduced pressure and increased volume within piston chamber 26. The reduction in pressure causes inspiratory pressure-responsive valve 14 and pressure-responsive bladder valve 12 to open, allowing the calibration gas to be substantially evacuated from bladder 18, e.g. down to 5–10 cm. of water, below atmospheric pressure. Spring-loaded valve 16 is preset to open only after bladder 18 is essentially collapsed. As springloaded valve 16 opens, atmospheric air passes therethrough, through conduit 15 and through valve 14 to mix with the calibration gas within piston chamber 26. The amount of air volume introduced into chamber 26 is determined by the stroke displacement of piston 30 in the upward (inhalation) phase of the piston cycle minus the amount of gas previously drawn from the bladder 18 (the calibration gas representing the simulated metabolic rate taking place in a biological subject). Typically, about 250–300 cc of calibration gas and about 700–750 cc of air are introduced into chamber 26 during the inhalation phase of the respiratory cycle.

During the downward phase of the pump cycle simulating exhalation, the reciprocating device 33 forces piston 30 towards the valved lower end of piston cylinder 25 to dotted line position A, and inspiratory valve 12 and spring-loaded valve 16 close. The decreasing volume of piston chamber 26 increases the pressure on the gases within until one-way pressure-responsive expiratory valve 35 opens. The forward motion of piston 30 evacuates the gases from piston chamber 26 so that the gases are released, via a corrugated conduit means 37, through mouthpiece interface 28, one-way pressure valve 60b, corrugated conduit 62 and thence into the subsequent stages of respiratory analysis system and equipment 40 being tested. A portion of the released gases may exit mouthpiece 28 by line 64.

As the piston 30 reaches the maximum position of exhalation (position A in FIG. 1), the cycle of the reciprocating device 33 reverses, thereby restarting the inhalation cycle as aforedescribed.

This cycle of inspiration and expiration of gases occurs repetitively and reproducibly. The volume displacement of the piston chamber 26 determines the simulated tidal volume (the volume of a single breath) and the rate of repitition of the cycling of the piston multiplied by the tidal volume will determine the minute ventilation of the lungs.

The volume of inlet and outlet gas mixture is controlled by the reciprocal power means 33 to piston rod 32. Since the calibration gas composition, as well as its flow rate, the atmospheric air composition, the tidal volume and, the cycling rate are all known, all parameters that are calculated by the analytical system can be directly compared. These parameters include breath-by-breath value determinations of tidal volume ($V_T$), ventilatory minute volume ($V_E$), respiratory frequency, (f), respiratory gas exchange ratio (R), $O_2$ consumption ($VO_2$) and $CO_2$ production ($VCO_2$). These parameters reflect directly on the fitness of biological subjects to be studied on the respiratory analysis devices.

Features of this invention combine calibration and evaluation procedures. Any quantity of respiratory or gas exchange variables can be chosen, executed at will and "on line" confronted with readings produced by respiratory processing equipment or setup, so that the readjustment and tuneup procedures can be performed quickly and precisely. As a result, the entire calibration procedure takes minutes instead of hours. The method and means of this invention also utilizes only about 25% of an otherwise required quantity of expensive calibrating gas mixtures, as compared with Boutellier et al, and effects a very substantial saving in manpower and cost over manual methods of calibration.

The rotameter and one-way valves utilized in the calibration system of this invention are inexpensive, simple and reliable. Further, the valving means between the bladder 18 and conduit means 29 may be further simplified as by elimination of the spring loaded valve 16, and replacing it with a simple orifice, in which case there will be a simultaneous air and calibration gas inflow to piston chamber 26 during the upward stroke of piston 30. Rotameter 20 and valve 13 controlling flow from calibration gas cylinder 11 may be replaced with gas dispenser devices of many other types. Further modifications of the method and means of this invention will be obvious to those skilled in the art.

I claim:

1. Apparatus for simulating the respiratory cycle of a biological subject which comprises:
   a piston chamber;
   a piston slidably movable within said piston chamber;
   power means for moving said piston within said piston chamber in a reciprocal forward and backward cycle of movement, each complete cycle of movement of said piston corresponding to an inhalation phase and an exhalation phase of a single respiratory cycle;
   a first container means adapted to contain calibration gas;
   a first conduit means;
   a first valve means for introducing, via said first conduit means, a known volume of said calibration gas to said piston chamber from said first container means during said inhalation phase of each of said cycle of piston movement;
   a second conduit means;
   a second valve means for introducing, via said second conduit means, a known volume of air to said piston chamber for admixture with said calibration gas, in said piston chamber during said inhalation phase of each said cycle of piston movement, both said calibration gas and air introduced into said piston chamber during said inhalation phase, simulating inhalation and a given metabolic rate;
   a third valve means for expelling said admixed air and calibration gases from said piston chamber during said exhalation phase of said cycle of piston movement, said expelling of said gases simulating exhalation and a predetermined metabolic rate; and
   a third conduit means for communicating said expelled gases, resulting from a series of complete cycles of movement of said piston, into a respiratory analysis system for calibration and adjustment of said respiratory analysis system with reference to the known compositions and volumes of gas expelled from said piston chamber.

2. The apparatus of claim 1 which includes only a single piston chamber, and a single piston slidably moveable therewithin.

3. The apparatus of claim 1 wherein said first container means is a flexibly-walled collapsible bladder or bellows.

4. The apparatus of claim 1 wherein said first container means is provided with a flow communication means adapted to communicate with a tank means containing said calibration gas, in bulk form.

5. The apparatus of claim 1 in which said piston is variable in frequency and extent of movement within said piston chamber.

6. The apparatus of claim 1 wherein said first, second and third valve means are one-way pressure valves.

7. The apparatus of claim 1 in which said second valve means automatically opens after said known volume of said calibration gas has been evacuated from said bladder and introduced into said position chamber.

8. The apparatus of claim 1 in which said second valve means opens as said known volume of said calibration gas is introduced into said piston chamber.

9. The apparatus of claim 1 wherein said second and third conduit means include elongated corrugated tubing.

10. The apparatus of claim 1 wherein said first valve means opens in response to the suction created in the piston chamber during the respiratory phase of each cycle.

11. The apparatus of claim 1 wherein said second valve means is pressure-responsive to open when said calibration gas pressure is below a pre-determined pressure level corresponding to a substantially evacuated volume of calibration gas in said first container.

* * * * *